United States Patent
Terstappen et al.

(10) Patent No.: US 6,858,384 B2
(45) Date of Patent: *Feb. 22, 2005

(54) PHAGE ANTIBODIES

(75) Inventors: Leon W M M Terstappen, Huntingdon Valley, PA (US); Ton Logtenberg, Utrecht (NL)

(73) Assignee: Crucell Holland B.V., CN Leinden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 09/865,048

(22) Filed: May 24, 2001

(65) Prior Publication Data

US 2002/0132228 A1 Sep. 19, 2002

Related U.S. Application Data

(63) Continuation of application No. 09/085,072, filed on May 26, 1998, now Pat. No. 6,265,150, which is a continuation-in-part of application No. 08/932,892, filed on Sep. 18, 1997, now abandoned, which is a continuation of application No. 08/483,633, filed on Jun. 7, 1995, now abandoned.

(51) Int. Cl.$^7$ .............................. C12Q 1/70; C12Q 1/68; C12P 21/04; C12N 15/00; C07K 1/00
(52) U.S. Cl. .............................. 435/5; 435/6; 435/69.6; 435/69.9; 435/320.1; 435/332; 436/547; 530/387.1; 530/395
(58) Field of Search .............................. 435/5, 6, 69.6, 435/69.9, 70.1, 71.1; 436/546, 547; 530/387.1, 395, 412

(56) References Cited

U.S. PATENT DOCUMENTS 6,265,150 B1 * 7/2001 Terstappen et al.

FOREIGN PATENT DOCUMENTS

| EP | 0610774 A1 | * | 8/1994 |
| WO | WO 94/26787 | * | 11/1994 |

OTHER PUBLICATIONS de Kruif (PNAS USA Apr. 1995;92:3938–3942).*
Winter et al (Annu. Rev. Immunol. 1994;12:433–455).*

* cited by examiner

Primary Examiner—G Nickol
Assistant Examiner—C Yaen
(74) Attorney, Agent, or Firm—Hoffmann & Baron, LLP; Irving N. Feit

(57) ABSTRACT

Peripheral blood leucocytes incubated with a semi-synthetic phage antibody library and fluorochrome-labeled CD3 and CD20 antibodies were used to isolate human single chain Fv antibodies specific for subsets of blood leucocytes by flow cytometry. Isolated phage antibodies showed exclusive binding to the subpopulation used for selection or displayed additional binding to a restricted population of other cells in the mixture. At least two phage antibodies appeared to display hitherto unknown staining patterns of B lineage cells. This approach provides a subtractive procedure to rapidly obtain human antibodies against known and novel surface antigens in their native configuration, expressed on phenotypically defined subpopulations of cells. Importantly, this approach does not depend on immunization procedures or the necessity to repeatedly construct phage antibody libraries.

7 Claims, No Drawings

PHAGE ANTIBODIES

This application is a continuation of application Ser. No. 09/085,072 filed May 26, 1998, now U.S. Pat. No. 6,265,150, which is a continuation in part of application Ser. No. 08/932,892 filed Sep. 18, 1997, now abandoned, which is a File-Wrapper-Continuation of Ser. No. 08/483,633 filed Jun. 7, 1995, now abandoned, both of which are incorporated herein by reference.

BACKGROUND OF THE INVENTION

The construction of libraries of fragments of antibody molecules that are expressed on the surface of filamentous bacteriophage and the selection of phage antibodies (Phabs) by binding to antigens have been recognized as powerful means of generating new tools for research and clinical applications. This technology, however, has been mainly used to generate Phabs specific for purified antigens that are available in sufficient quantities of solid-phase dependent selection procedures. The effectiveness of such Phabs in biochemical and functional assays varies; typically, the procedure used to select Phabs determines their utility.

Typically, many antigens of interest are not available in pure form in very large quantities. This clearly limits the utility of Phabs in binding such materials for research and clinical applications. Further, the utility of Phabs in such applications is directly proportional to the purity of the antigens and purification methods to assure the specificity of the isolate Phabs. Human monoclonal antibodies that bind to native cell surface structures are expected to have broad application in therapeutic and diagnostic procedures. An important extension of phage antibody display technology would be a strategy for the direct selection of specific antibodies against antigens expressed on the surface of subpopulations of cells present in a heterogenous mixture. Ideally, such antibodies would be derived from a single highly-diverse library containing virtually every conceivable antibody specificity.

SUMMARY OF INVENTION

A library was constructed from 49 human germline $V_H$ genes fused to a $J_H4$ gene and partly randomized CDR3 regions varying in length between 6 and 15 amino acids. The CDR3 regions were designated to contain short stretches of fully randomized amino acid residues flanked by regions of limited variability. Residues in the latter portion of CDR3 were selected based on their frequent occurrence in CDRs (complementarity-determining regions) of natural antibody molecules, random CDR3 with an increased frequency of clones producing functional antigen binding sites. The synthetic $V_H$ segments were combined with seven different $V_L$ genes and expressed as geneIII-scFv fragments on the surface of phage, resulting in a library of $3.6 \times 10^8$ clones. This library was used to isolate monoclonal phage antibodies (MoPhabs) to a variety of different structures (haptens, proteins and polysaccharides) by selection on solid phase-bound antigen.

Further, MoPhabs were also isolated by flow cytometry, resulting in MoPhabs specific for subpopulations of cells present in a heterogenous mixture. These antibodies detect known and novel structures on various populations of blood and fetal bone marrow cells.

DETAILED DESCRIPTION OF INVENTION

The phage antibodies of the instant invention are obtained from a library of phage antibodies which possess specificity for a plurality of antigens. In practice, such libraries can be obtained from a variety of sources or constructed by known methods. A method particularly useful for constructing such libraries is described in paper by G. Winter, et al., *Annual Reviews of Immunology*, 12, 433–455 (1994), which is incorporated by references.

The library is then admixed with the antigens (as used herein, antigen shall be inclusive of haptens and antigen analogs) of interest and the phage antibodies bound to these antigens are then isolated. The procedure may be repeated until a population of phage antibodies having the desired specificity(ies) is obtained, and the isolated phage antibodies may then be cloned by conventional methods known to those in the art.

In a preferred embodiment, the phage antibody library is admixed with a cell mixture labeled with a fluorescent labeled antigen, or a plurality of antigens each labeled with a different fluorescent label, and sorted by flow cytometry. Preferred labels include phycoerythrin (PE), PerCP, and fluorescein isothiocyanate (FITC). The phage antibodies bound to cells, thus obtained, can be eluted. The phage antibodies (phages that express antibody specificities of interest) can then be cloned by conventional techniques to obtain a plurality of phage antibodies having high specificity for single antigens.

EXAMPLES

The following examples illustrate certain preferred embodiments of the instant invention, but are not intended to be illustrative of all embodiments.

Example 1

Library Construction

The semi-synthetic Phab library was constructed essentially as described in Hoogenboom and Winter, J. Mol. Biol. 227, 381–388 (1992) and Nissim et al. *EMBO* 13,692–698 (1994). Briefly, degenerate oligonucleotides were used to add synthetic CDR3 regions to a collection of 49 previously cloned germline $V_H$ genes. Subsequently, these in vitro 'rearranged' $V_H$ genes were cloned into a collection of pHENI phagemid-derived vectors containing 7 different light chain V regions, fused in frame to the gene encoding the phage minor capsid protein geneIII. Introduction of these constructs into bacteria results, in the presence of helper phage, in the expression of scFv antibody fragments as geneIII fusion proteins on the surface of bacteriophage.

Plasmid DNA containing the $V_\kappa 3$ gene expressed in EBV-transformed cell line was amplified with primers $V_\kappa 3$LINK and $J_\kappa 4$B to introduce NcoI and XhoI restriction sites and the (G4S) linker sequence. Amplified product was cloned into the pHEN1 phagemid vector using NcoI and XhoI resulting in pHEN1-$V_\kappa 3$. Total RNA was isolated from fetal bone marrow B lymphocytes, converted to cDNA by oligo-dT priming and amplified by PCR using $V_\kappa 1$, $V_\kappa 2$, $V_\kappa 4$, $V_\lambda 1$ and $V_\lambda 2$ gene family-specific primers. All PCR reactions were carried out in a volume of 50 $\mu$l with 250 $\mu$M dNTPs, 20 pmol of each primer and 0.2 units of Taq DNA polymerase (Supertaq, HT biotechnology Ltd. Cambridge, UK) in the manufacturer recommended buffer. PCR reactions consisted of 25 cycles of 1 minute at 94° C., 1 minute at 58° C. and 2 minutes at 72° C.). PCR amplified products were digested with SacI and NotI and ligated in the pHEN1-$V_\kappa 3$ vector digested with the same enzymes. This resulted in the construction of 7 pHEN 1-derived vectors, each containing a rearranged member of the $V_\kappa 1$, $V_\kappa 2$, $V_\kappa 3$, $V_\kappa 4$, $V_\lambda 1$, $V_\lambda 2$ and $V_\lambda 3$ gene families, the scFv linker and restriction sites XhoI and NcoI for cloning of the heavy chain library. Nucleotide sequences of the $V_L$ genes appear in the EMBL, Genbank and DDBJ Nucleotide Sequence Databases under accession numbers X83616 and X83712–X83714.

PCR primers were designed to fuse a bank of 49 germline $V_H$ genes (Tomlinson et al., *J. Mol. Biol.* 227, 776–798 (1992)) to CDR3 regions, varying in length from 6 to 15 residues, and a $J_H 4$ gene segment. Template, consisting of 0.5 ng of a mixture of plasmids encoding genes from a single $V_H$ gene family, was amplified using the $V_H$ family based primers VHBackSfi (Marks et al., *J. Mol. Biol.* 222, 581–597 (1991)) and one of the CDR3 primers. PCR products of each amplification encoding a differently-sized HCDR3 loop were digested with XhoI and NcoI and cloned into the pHEN1-$V_\lambda 1$ vector. This resulted in a phagemid library of $1.2 \times 10^8$ clones. Plasmid DNA from this library was digested with XhoI-NcoI and the synthetic $V_H$ regions were cloned into the other pHENI-light chain vectors, resulting in seven libraries, each varying in size between $2 \times 10^7$ and $1.2 \times 10^8$ clones. The seven libraries were rescued individually (Marks et al., *EMBO* 12, 725–734 (1993)) using helper phage VCS-M13 (Stratagene) and finally combined to form a single library of $3.6 \times 10^8$ clones.

Example 2
Selection of Phage Antibodies

The phages were panned for binding to antigen-coated immunotubes (Nunc Maxisorp; Marks et al. *J. Mol. Biol.* 222, 581–597 (1991) using the following antigens: dinitrophenol (DNP) coupled to BSA, tetanus toxoid (TTX), tyraminated Group B Streptococcal type III capsular polysaccharide (GBS), human surfactant protein A (spA; Hawgood, *Pulmonary Surfactant. From Molecular Biology to Clinical Practice*. Elsevier Science Publishers, pp. 33–54 (1992), human thyroglobulin (Tg; Logtenberg et al., *J. Immunol.* 136,1236–1240 (1986)), human Von Willebrand Factor (VWF), human VWF fragment A2, a purified human IgG paraprotein, a recombinant protein corresponding to the HMG domain of T cell-specific transcription factor TCF-1 (HMG, van Houte et al, *J. Biol. Chem.* 268, 18083 (1993), a deletion mutant of the epithelial glycoprotein EGP-2 ($\delta$EGP-2; Helfrich et al., *Int. J. Cancer, Suppl.* 8,1. (1994), the extracellular portion of human ICAM-1, (Hippenmeyer et al. *Bio. Technology* 11, 1037 (1993), an uncharacterized DNA binding protein isolated from a cDNA library and expressed as a maltose binding protein (MBP) fusion protein (BLT1/MBP), and the human homeobox protein PBXla (Monica et al. *Mol. Cell. Biol.* 11, 6149–6157 (1991). All antigens were coated overnight at room temperature at a concentration of 10 ug/ml in PBS (DNP-BSA, GBS, Tg, VW, A2, TTX, ICAM-1, BLT1/MBP, PBX1a) or 50 mM $NaHCO_3$ pH 9.6 (IgG, spA, HMG, $\delta$EGP-2).

To target selection of Phabs to a desired portion of a molecule, phage selections were performed on solid phasebound BLT1/MBP fusion protein as described in the standard protocol with the addition of 6 $\mu$g/ml soluble MBP to the Phab-milkpowder mixture during panning. In order to obtain Phabs capable of discriminating between two highly homologous proteins, selections on immunotube-coated full-length PBX1a were carried out according to the standard protocol in the presence of 5 $\mu$g/ml full-length recombinant PBX2 protein during panning (Monica et al., Mol. Cell. Biol 11, 6149–6157 (1991).

Example 3
Selection of Phage Antibodies by Cell Sorting

Venous blood was diluted 1:10 in 0.8% $NH_4Cl$/0.08% $NaHCO_3$/0.08% EDTA (pH 6.8) to remove erythrocytes and the nucleated cells were pelleted and washed once in PBS/1% BSA. Approximately $10^{13}$ phage antibody particles were blocked for 15 minutes in 4 ml 4% milkpowder in PBS (MPBS). $5 \times 10^6$ leucocytes were added to the blocked phages and the mixture was slowly rotated overnight at 4° C. The following day, cells were washed twice in 50 ml ice-cold PBS/1% BSA. The pelleted cells were resuspended in 50 $\mu$l of CD3-PerCP and 50 $\mu$l of CD20-FITC and after a 20 minute incubation on ice, cells were washed once with 1% BSA/PBS and resuspended in 500 $\mu$l ice-cold PBS/1% BSA. Cell sorting was performed on a FACSvantage®. For each subpopulation, $10^4$ cells were sorted in 100 $\mu$l PBS.

Example 4
Propagation of Selected Phases

Phages were eluted from the cells by adding 150 $\mu$l 76 mM citric acid pH 2.5 in PBS and incubation for 5 minutes at room temperature (RT). The mixture was neutralized with 200 $\mu$l 1 M Tris/HCl, pH 7.4. Eluted phages were used to infect E'Coli X11-Blue and the bacteria were plated on TYE medium containing the appropriate antibiotics and glucose. Bacterial colonies were counted, scraped from the plates and used as an inoculum for the next round of phage rescue.

Example 5
Preparation of Monoclonal Phage Antibodies and scFy Fragments and Immunofluorescent Analysis Phages were prepared from individual ampicillin resistant colonies grown in 25 ml 2TY medium, purified by polyethylene glycol precipitation, resuspended in 2 ml PBS, filtered (0.45 $\mu$M) and stored at 4° C. until further use. ScFv fragments were produced in *E Coli* non-suppressor strain SF 110 that is deficient in the proteases degP and ompT. In our experience, the stability of scFv produced in SF110 is superior to that of scFv produced in HB2151 commonly used for this purpose.

For staining of leucocytes, 100 $\mu$l MoPhab was blocked by adding 50 $\mu$l 4% MPBS for 15 minutes at RT. $5 \times 10^5$ leucocytes in 50 $\mu$l PBS/1% BSA were added and incubated on ice for 1 hour. The cells were washed twice in ice-cold PBS/1% BSA. To detect cell-bound phages, the cells were incubated in 10 $\mu$l of 1/200 diluted sheep anti-M13 polyclonal antibody (Pharmacia, Uppsala. Sweden), washed twice and incubated in 10 $\mu$l of 20 $\mu$g/ml PE-labeled donkey anti-sheep polyclonal antibody (Jackson Immunoresearch, West Grove, Pa.), each for 20 minutes on ice. The cells were washed and incubated in 10 $\mu$l each of CD3-FITC and CD20-PerCP monoclonal antibodies. When cells were strained with purified scFv fragments, second and third step reagents consisted of the anti-myc tag-specific antibody 9E10 and FITC- or PE-labeled goat anti-mouse antibodies. After a single final wash, the cells were resuspended in 0.5 ml PBS/1%BSA and analyzed by FACS.

Fetal bone marrow was from aborted fetuses (16–22 weeks gestation) and used following the guidelines of the institutional review board of Stanford Medical School Center on the use of human subjects in medical research. Bone marrow cells were obtained by flushing intramedullary cavities of the femurs with RPMI 1640 medium. Pelleted cells were treated with the hypotonic $NH_4Cl$ solution to remove erythrocytes. $10^6$ fetal bone marrow cells were stained with MoPhabs T1, B9, and B28 in combination with a panel of fluorochrome-labeled MoAbs. The panel includes CD3 (Leu 4B PerCP), CD4 (Leu FITC), CD8 (Leu2a APC), CD 10 (anti Calla FITC; all from Becton Dickinson Immunocytometry Systems, San Jose, Calif.), and FITC-conjugated goat anti-human, $\mu$, $\delta$, and $\kappa$ chain-specific polyclonal antibodies (Southern Biotechnologies, Ala.).

Example 6
Specificity of Isolated MoPhabs $5 \times 10^6$ erythrocyte-lysed peripheral blood cells from a healthy individual were incubated with the phage library and subsequently stained with CD3 PerCP and CD20 FITC labeled monoclonal antibodies (MoAbs). The population was run on a flow cytometer.

$10^4$ cells of each population were sorted and the phages bound to the isolated cells were eluted from the cell surface. The number of clones obtained after the first round of selection varied between 320 and 1704. The number of phage clones obtained roughly was inversely correlated with the frequency of the cell population in the blood sample as shown in Table 1.

TABLE 1

| | # MoPhabs | | | |
|---|---|---|---|---|
| Sorted Population | Round 1 | Round 2 | # Pos. Clones | # Staining Profiles |
| 'all' leucocytes | 640 | 980 | 15/15 | 1 |
| eosinophils | 1280 | 390 | 11/15 | 2 |
| T-cells (CD3$^+$) | 320 | 3330 | 15/15 | 2 |
| B-cells (CD20$^+$) | 1704 | 6000 | 10/16 | 3 |

The second round of selection resulted in a modest increase in the number of phages eluted from the cells in most but not all cases as shown in Table 1.

The phages eluted from the sorted cells were expanded as individual libraries and used in a second round of selection employing the same procedure. Finally, MoPhabs were prepared from individual colonies obtained after the second round of selection.

The binding properties of 15 MoPhabs from each sorted population was analyzed by incubation with peripheral blood leucocytes followed by incubation with secondary anti-phage PE-labeled antibody and CD20 FITC and CD3 PerCP. After two rounds of selection, between 63% and 100% of the MoPhabs were found to display binding activity to leucocytes, see Table 1.

Staining profiles were obtained for a negative control MoPhab, a MoPhab derived from sorting 'all' leucocytes, two eosinophil-derived MoPhavs (E1/E2), two T cell derived MoPhabs 9T1fF2) and two B cell derived MoPhabs (B9/B28). ScFv fragments were produced from each MoPhab clone. For all clones, identical results were obtained for whole phage antibodies and isolated scFv fragments, albeit some loss of signal intensity was observed when using the latter. The 15 MoPhAbs selected on 'all' leucocytes showed identical staining patterns: all granulocytes, eosinophils, and monocytes stained homogeneously bright. All the T lymphocytes stained but with varying intensity. Strikingly, no binding to B lymphocytes was observed. Among the 15 MoPhAbs selected for binding to eosinophils, two staining patterns were discernable. Both MoPhabs bound to all eosinophils and monocytes; the staining profile of granulocytes differed between both MoPhabs. MoPhab E2 reacted with the majority of T cells, whereas virtually no staining of T cells was observed with MoPhab E1. Conversely, MoPhab E2 did not bind to B cells while MoPhab E1 stained virtually all B cells. Two staining patterns could be distinguished among the 12 MoPhabs selected for binding to T lymphocytes. MoPhab T2 dimly stained a subpopulation of B cells, T cells and granulocytes but not monocytes and eosinophils. MoPhab T 1 exclusively and brightly stained a subpopulation of T lymphocytes comprising approximately 50% of CD3$^+$ cells. Finally, among MoPhabs selected from B cells, three staining patterns were distinguishable: approximately 50% of the peripheral blood B cells stained with MoPhab B9, MoPhab B28 stained all CD20$^+$ peripheral blood B cells, whereas MoPhab B 11 stained virtually all leucocytes.

MoPhabs TI, B9 and B28 were selected for further characterization. In four color staining experiments with CD3, CD4, CD8 and T 1 antibodies, T 1 was shown to bind to CD8$^+$ cells and not to CD4$^+$ cells. Immunofluorscent staining of COS cells transiently transfected with cDNAs encoding the CD8$\alpha$ chain, the CD8$\beta$ chain or both demonstrated that MoPhAb T1 recognized cells expressing the CD8$\alpha\alpha$ homodimer. We conclude that T1 recognizes an epitope encoded by the CD8$\alpha$ chain.

Triple-staining of B9 with CD20 and antisera specific for the immunoglobulin $\mu$, $\delta$, $\gamma$, $\alpha$, $\kappa$, and $\lambda$ chains revealed that B9 marker expression did not concur with any of the Ig isotypes. Triple-staining of purified tonsil B cells with MoPhab B9 or B28, CD 19, and CD 10 or $\mu$ heavy chain specific antibodies confirmed that B28 binds to all and B9 binds to a subpopulation of CD 19$^+$ tonsil B cells. Germinal center B cells (CD19$^+$/CD10$^+$) uniformly lack the antigen recognized by MoPhab B9. In human bone marrow, the CD 19 marker is expressed from the earliest pro-B cell to the virgin, surface IgM$^+$ B cell stage. Triple staining of fetal bone marrow cells with CD 19, sIgM and B9 or B28 demonstrated that B9 and B28 are not expressed during B lineage differentiation. We conclude that the structures detected by the B9 and B28 MoPhabs are expressed at a very late stage of B cell development, presumably after newly generated sIgM+B cells have left the bone marrow. To our best knowledge B cell-specific markers with such expression patterns have not been described previously.

Nucleotide sequence analysis was used to established $V_H$ and $V_L$ gene utilization and heavy chain CDR3 composition encoding the scFv antibodies obtained from the sorted subpopulations as shown in Table II.

TABLE II $V_H$ and $V_L$ gene utilization and deduced amino acid sequence of CDR3 regions of selected MoPhabs.

| MoPhab | CDR3 | $V_H$ | $V_L$ |
|---|---|---|---|
| A1 | RMRFPSY | DP32 | V$\lambda$3 |
| E1 | RLRSPPL | DP32 | V$\lambda$2 |
| E2 | RAWYTDSFDY | DP45 | V$\kappa$1 |
| T1 | KWLPPNFFDY | DP32 | V$\kappa$3 |
| T2 | RSTLADYFDY | DP69 | V$\lambda$3 |
| B9 | KGVSLRAFDY | DP31 | V$\kappa$1 |
| B28 | RGFLRFASSWFDY | DP32 | V$\lambda$3 |

ScFv derived from different clones with the same staining profile showed identical nucleotide sequences of CDR3 regions. The MoPhabs with different staining patterns were encoded by various combinations of $V_H$ and $V_L$ chains, with an overrepresentation of the DP32 gene fragment, and comprised CDR3 loops varying in length between 6 and 12 amino acids.

It is apparent that many modifications and variations of this invention as hereinabove set forth may be made without departing from the spirit and scope thereof. The specific embodiments are given by way of example only and the invention is limited only by the terms of the appended claims.

What is claimed is:

1. A method for obtaining a phage particle comprising an antibody fragment directed against an antigen associated with the surface of target cells in a heterogeneous cell population, wherein said heterogeneous cell population comprises non-target cells and target cells in a heterogeneous mixture, and wherein said non-target cells and/or target cells are detectably labeled, the method comprising:

(a) providing a library of phage particles that express antibody fragments on the surface of the phage particles;

(b) incubating said library of phage particles with said heterogeneous cell population under conditions that allow binding of the antibody fragment expressed on the surface of the phage particles to said antigen associated with said target cells;

(c) separating said target cells and phage particles bound therewith from phage particles not bound to said target cells; and (d) recovering the phage particles bound to the target cells.

2. A method according to claim 1, wherein the separating of said target cells and phage particles bound therewith from phage particles not bound to said target cells is accomplished by flow cytometry.

3. A method according to claim 1, further comprising isolating antibody fragments that bind to said target cells.

4. A method according to claim 1, wherein said detectably labeled cells are labeled with a fluorescent label.

5. A method according to claim 4, wherein said fluorescent label is a fluorescein label.

6. A method according to claim 1, further comprising repeating steps (b) through (d).

7. A method according to claim 1, wherein the library of phage particles comprises phage particles expressing Fab or single chain Fv (scFv) antibody fragments.

* * * * *

UNITED STATES PATENT AND TRADEMARK OFFICE
CERTIFICATE OF CORRECTION

PATENT NO. : 6,858,384 B2
DATED : June 23, 2005
INVENTOR(S) : Terstappen et al.

It is certified that error appears in the above-identified patent and that said Letters Patent is hereby corrected as shown below:

Column 2,
Line 64, now reads "of 7 pHEN 1-derived ...", and should read -- of 7 pHEN1-derived... --.

Column 4,
Line 14, now reads "Phases ....", and should read -- Phages... --.

Signed and Sealed this

Twenty-third Day of August, 2005

JON W. DUDAS
*Director of the United States Patent and Trademark Office*

UNITED STATES PATENT AND TRADEMARK OFFICE
CERTIFICATE OF CORRECTION

PATENT NO. : 6,858,384 B2
DATED : February 22, 2005
INVENTOR(S) : Terstappen et al.

It is certified that error appears in the above-identified patent and that said Letters Patent is hereby corrected as shown below:

Column 2,
Line 64, now reads "of 7 pHEN 1-derived …", and should read -- of 7 pHEN1-derived… --.

Column 4,
Line 14, now reads "Phases ….", and should read -- Phages… --.

This certificate supersedes Certificate of Correction issued August 23, 2005.

Signed and Sealed this

Eighteenth Day of October, 2005

JON W. DUDAS
*Director of the United States Patent and Trademark Office*